US008338629B2

(12) United States Patent
Byun et al.

(10) Patent No.: US 8,338,629 B2
(45) Date of Patent: Dec. 25, 2012

(54) ORGANOMETALLIC PRECURSOR FOR METAL FILM OR PATTERN AND METAL FILM OR PATTERN USING THE PRECURSOR

(75) Inventors: Young Hun Byun, Yongin-si (KR); Tatsiana Kuzniatsova, Yongin-si (KR); Hye Yeon Yang, Seoul (KR)

(73) Assignee: Samsung Electronics Co., Ltd. (KR)

( * ) Notice: Subject to any disclaimer, the term of this patent is extended or adjusted under 35 U.S.C. 154(b) by 802 days.

(21) Appl. No.: 12/399,344

(22) Filed: Mar. 6, 2009

(65) Prior Publication Data

US 2010/0071587 A1    Mar. 25, 2010

(30) Foreign Application Priority Data

Sep. 19, 2008 (KR) .................. 10-2008-0092157

(51) Int. Cl.
*C07F 15/00* (2006.01)
*C07F 1/00* (2006.01)
*C23C 20/00* (2006.01)

(52) U.S. Cl. .......... 556/36; 556/110; 556/137; 556/138; 106/1.18

(58) Field of Classification Search .................. 556/36, 556/110, 137, 138; 106/1.18
See application file for complete search history.

(56) References Cited

U.S. PATENT DOCUMENTS

| 4,781,980 | A | 11/1988 | Yoshitake et al. | |
| 4,789,411 | A | 12/1988 | Eguchi et al. | |
| 7,081,214 | B2 | 7/2006 | Matsuba et al. | |
| 2001/0012869 | A1* | 8/2001 | Fukushima et al. | 524/588 |
| 2002/0160103 | A1* | 10/2002 | Fukunaga et al. | 427/125 |
| 2006/0254378 | A1 | 11/2006 | Akutagawa | |
| 2006/0261816 | A1 | 11/2006 | Rocher et al. | |
| 2007/0170403 | A1 | 7/2007 | Conaghan et al. | |

FOREIGN PATENT DOCUMENTS

| JP | 2007-042301 | 2/2007 |
| KR | 10-0784762 A | 3/2007 |
| WO | 02/31068 | 4/2002 |

OTHER PUBLICATIONS

Koksharova et al., Russian Journal of Coordination Chemistry, vol. 27, No. 10, pp. 738-740 (2001).*
G. R. Burns, Inorganic Chemistry, vol. 7, No. 2, pp. 277-283 (1968).*

* cited by examiner

*Primary Examiner* — Porfirio Nazario Gonzalez
(74) *Attorney, Agent, or Firm* — Cantor Colburn LLP (57) ABSTRACT

Provided are an organometallic precursor, wherein a carboxyhydrazide compound is coordinated to a central metal, and a metal film or pattern using the precursor. By using the organometallic precursor, highly pure metal films or patterns can be obtained through a simple low-temperature process.

17 Claims, 1 Drawing Sheet

US 8,338,629 B2

ORGANOMETALLIC PRECURSOR FOR METAL FILM OR PATTERN AND METAL FILM OR PATTERN USING THE PRECURSOR

CROSS-REFERENCE TO RELATED APPLICATION

This application claims priority to Korean Patent Application No. 10-2008-92157, filed on Sep. 19, 2008, and all the benefits accruing therefrom under 35 U.S.C. §119, the contents of which in its entirety are herein incorporated by reference.

BACKGROUND

1. Field

This disclosure relates to an organometallic precursor for forming metal films or patterns, and to metal films or patterns that comprise the organometallic precursor. More specifically, this disclosure relates to an organometallic precursor wherein a carboxyhydrazide compound is coordinated to a central metal atom. This disclosure also relates to metal films or patterns that comprise the organometallic precursor.

2. Description of the Related Art

With the miniaturization of electric devices and their integration into devices such as, for example, printed circuit boards ("PCBs"), solar cells, radio frequency identification ("RFID") systems and liquid crystal display devices, metal line patterns formed on a substrate have gradually become finer in size. In order to form such fine metal line patterns, photolithography, electroplating, soft-lithography and ink-jet printing are generally used.

In particular, flexible displays or thin film transistor-liquid crystalline displays ("TFT-LCDs"), which have been the focus of intense interest, require a technique for forming high-quality gate insulating films and low-resistance source/drain electrodes to produce high-quality images on a large screen. As a result of the use of these high-quality gate insulating films, it is desirable to have methods for forming films that have disposed on them fine metal line patterns that have a high electrical conductivity. It is further desirable for the method used to manufacture the film to be operative at a low temperature and to permit control of the thickness of the film as well as the thickness of the metal line patterns.

SUMMARY

Disclosed herein are embodiments relating to an organometallic precursor that includes a ligand that is coordinated to a metal, where the ligand has a reducing capability.

Disclosed herein too are embodiments relating to a composition including the organometallic precursor and metal nanoparticles.

Disclosed herein too are embodiments relating to a composition including a compound with reducing ability and an organometallic compound.

Disclosed herein too are embodiments relating to a method for forming metal films or patterns through a simple low-temperature process using the organometallic precursor and the composition that includes the organometallic precursor.

Disclosed herein too are embodiments relating to metal films or patterns produced from the organometallic precursor and the compositions that include the organometallic precursor.

Disclosed herein too are embodiments relating to an organometallic precursor for forming a metal film or pattern, which is represented by Formula 1 below:

wherein M is a transition metal; L' is a neutral ligand; X is an anion coordinated or uncoordinated to M; m is an integer of 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q are not zero; L is a carboxyhydrazide compound coordinated to a metal, which is represented by Formula 2:

wherein $R_1$, $R_2$, $R_3$, $R_4$, $R_5$, and $R_6$ are each independently hydrogen, a substituted or unsubstituted $C_1$-$C_{30}$ alkyl group or a substituted or unsubstituted $C_6$-$C_{30}$ aryl group; G is oxygen (O), sulfur (S) or $NR_7$, in which N is nitrogen and $R_7$ is hydrogen, a substituted or unsubstituted $C_1$-$C_{30}$ alkyl group or a substituted or unsubstituted $C_6$-$C_{30}$ aryl group; and n is an integer of about 1 to about 40, with the proviso that when n is about 2 or higher, L may be identical to or different from each other.

Disclosed herein too are embodiments relating to a composition for forming a metal film or pattern, the composition including the organometallic precursor represented by Formula 1 and metal nanoparticles.

Disclosed herein too are embodiments relating to a composition for forming a metal film or pattern, including the carboxyhydrazide compound represented by Formula 2 above and a metal compound represented by Formula 3:

wherein M, L', X, m, p and q are defined as above.

Disclosed herein too are embodiments relating to a method for forming a metal film or pattern using the organometallic precursor and the composition that includes the organometallic precursor.

Disclosed herein too are embodiments relating to a metal film or pattern produced from the organometallic precursor and the composition that includes the organometallic precursor.

BRIEF DESCRIPTION OF THE DRAWINGS

Exemplary embodiments will be more clearly understood from the following detailed description taken in conjunction with the accompanying drawing, in which.

DETAILED DESCRIPTION

Hereinafter, a detailed description will be given of exemplary embodiments with reference to the accompanying drawings.

It will be understood that when an element or layer is referred to as being "on," "interposed," "disposed," or "between" another element or layer, it can be directly on, interposed, disposed, or between the other element or layer or intervening elements or layers may be present.

It will be understood that, although the terms first, second, third, and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, first element, component, region, layer or section discussed below could be termed second element, component, region, layer or section without departing from the teachings of the disclosure.

As used herein, the singular forms "a," "an" and "the" are intended to comprise the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In the drawings, the thickness of layers and regions are exaggerated for clarity.

In one embodiment, an organometallic precursor for forming metal films or patterns is represented by Formula 1 below:

$$L_n M_m L'_p X_q \quad (1)$$

wherein M is a transition metal; L' is a neutral ligand; X is an anion coordinated or uncoordinated to M; m is an integer of about 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q are not zero; L is a carboxyhydrazide compound coordinated to a metal, which is represented by Formula 2:

wherein $R_1$, $R_2$, $R_3$, $R_4$, $R_5$, and $R_6$ are each independently hydrogen, a substituted or unsubstituted $C_1$-$C_{30}$ alkyl group or a substituted or unsubstituted $C_6$-$C_{30}$ aryl group; G is oxygen (O), sulfur (S) or $NR_7$, in which N is nitrogen, $R_7$ is hydrogen, a substituted or unsubstituted $C_1$-$C_{30}$ alkyl group or a substituted or unsubstituted $C_6$-$C_{30}$ aryl group; and n is an integer of about 1 to about 40, with the proviso that when n is about 2 or higher, L may be identical to or different from each other.

In Formula 1, M is a metal selected from the group consisting of silver (Ag), gold (Au), copper (Cu), palladium (Pd), platinum (Pt), osmium (Os), rhodium (Rh), cobalt (Co), nickel (Ni), cadmium (Cd), iridium (Ir) iron (Fe), and a combination comprising at least one of the foregoing metals. In an exemplary embodiment, M is selected from the group consisting of Ag, Au, Cu, and a combination comprising at least one of the foregoing metals.

In Formula 2, the substituent of $R_1$ to $R_7$ is selected from the group consisting of fluoro (—F), chloro (—Cl), bromo (—Br), iodo (—I), hydroxyl (—OH), nitrile (—CN), nitro (—NO$_2$), nitrate (—NO$_3$), nitroxyl, azide (—N$_3$), thiocyanate (—SCN), isothiocyanate, tetraalkylborate [—BR$_4$ in which R is methyl (Me), ethyl (Et) or phenyl (Ph)], tetrahaloborate [—BX$_4$, in which X is F or Br], hexafluorophosphate (—PF$_6$), triflate (CF$_3$SO$_3$—), tosyl (—Ts), sulfate (SO$_4^{2-}$), carbonate (CO$_3^{2-}$), thiol (—SH), carbonyl (—CO), epoxy, vinyl, alkoxy and ester groups.

In Formula 1, L' is a neutral ligand coordinated to a metal, which is a $C_1$-$C_{20}$ organic compound containing an electron-donating atom selected from nitrogen (N), phosphorus (P), arsenic (As), oxygen (O), sulfur (S), selenium (Se) and tellurium (Te). In one exemplary embodiment, L' is selected from the group consisting of amine, phosphine, phosphine, phosphine oxide, arsine, thiol, carbonyl, alkene, alkyne and arene compounds. In another exemplary embodiment, L' is selected from the group consisting of n-BuNH$_2$, (i-Pr)$_2$NH, NEt$_3$, [H$_2$N(CH$_2$)$_4$]$_2$NH, N[(CH$_2$)$_2$NH$_2$]$_3$, PEt$_3$, P(n-Bu)$_3$, pyrazole, imidazole, octanethiol and dodecanethiol.

In Formula 1, X is an anion that is operative to electrically neutralize a metal compound, which may be coordinated or uncoordinated to the metal compound. Specifically, X is a $C_1$-$C_{20}$ anion containing one or more elements selected from oxygen (O), nitrogen (N), sulfur (S), phosphorus (P), fluorine (F), chlorine (Cl), bromine (Br), iodine (I), antimony (Sb), boron (B), arsenic (As), bismuth (Bi), silicon (Si) and tin (Sn). Examples of X include OH$^-$, CN$^-$, NO$_2^-$, NO$_3^-$, halides (F$^-$, Cl$^-$, Br$^-$ or I$^-$), trifluoroacetate, isothiocyanato, tetraalkylborate (BR$_4^-$, where R is methyl, ethyl or phenyl), tetrahaloborate (BX$_4^-$, where X is F or Br), hexafluorophosphate (PF$_6^-$), triflate (CF$_3$SO$_3^-$), tosylate (Ts$^-$), sulfate (SO$_4^{2-}$), carbonate (CO$_3^{2-}$), thiocyanate (SCN), nitroxyl, azide (N$_3^-$), acetylacetonate, hydrozino benzoic acid (CO$_2$C$_6$H$_4$NHNH$_2^-$) and trifluoroantimonate (SbF$_6^-$).

In Formula 1, when n, p, or q is about 2 or higher, L, L' or X may be identical to or different from each other, and when there are two or more metals (m≧2), L, L' or X may serve as a ligand connecting the metals to each other.

Examples of organometallic precursors which can be represented by Formula 1 include Cu(NO$_3$)$_2$[H$_2$NHNCONHNH$_2$], Cu(NO$_3$)$_2$[H$_2$NHNCSNHNH$_2$], Cu(NO$_3$)$_2$(H$_2$NHNCONHNH$_2$) (NEt$_3$), Cu(SO$_4$)(H$_2$NHNCONHNH$_2$) (NEt$_3$), Cu(NO$_3$)$_2$(H$_2$NHNCSNHNH$_2$) (NH(n-Bu)$_2$), Cu(NO$_3$)$_2$[CO(NHNHCOCH$_3$)$_2$], Cu(NO$_3$)$_2$[H$_2$NHNCONHNHCOC$_8$H$_{17}$], Cu(NO$_3$)$_2$[CO(NHNHCOC$_8$H$_{17}$)$_2$], Ni(NO$_3$)$_2$[H$_2$NHNCONHNH$_2$], Ni(NO$_3$)$_2$[H$_2$NHNCSNHNH$_2$], (n-PrNH$_2$)AuCl$_3$[H$_2$NHNCONHNH$_2$], Au(CN) (NEt$_3$)[H$_2$NHNCSNHNH$_2$], and Au(acetate)[H$_2$NHNCONHNH$_2$].

Examples of carboxyhydrazide compounds which can be represented by Formula 2 include H$_2$NHNCONHNH$_2$, H$_2$NHNCSNHNH$_2$, CO(NHNHCOCH$_3$)$_2$, CO(NHNHCOC$_8$H$_{17}$)$_2$, and H$_2$NHNCONHNHCOC$_8$H$_{17}$.

As can be seen in the Formula (1), the organometallic precursors comprise carboxyhydrazide compounds that can be activated at lower temperatures that exhibit an ability to reduce the metallic compounds that they contact. The ability to be activated at lower temperatures permits the hydrogen of the carboxyhydrazide ligands to reduce metal compounds and to promote decomposition of the overall organometallic precursor, thereby obtaining only a pure metal, in which the organic moieties are cleaved from the organometallic precursor.

In one embodiment, in one method of manufacturing the organometallic precursor of Formula (1), a solvent is added dropwise to a metal compound represented by Formula 3 below. The metal compound of Formula (3) dissolves in the solvent to form a metal compound solution. The carboxyhydrazide compound of Formula 2 is then dissolved in the same or different solvent. The solution containing the carboxyhydrazide compound of Formula (2) is then added to the metal compound solution accompanied by stirring at room temperature and removing the solvents.

$$M_m L'_p X_q \quad (3)$$

wherein M, L', X, m, p and q are defined as above.

Examples of useful solvents include acetonitrile, toluene, methyl isobutyl ketone, acetone, tetrahydrofuran, propylene glycol methyl ether acetate, isopropyl alcohol, water, or a combination comprising at least one of the foregoing solvents.

Examples of metal compounds that can be represented by Formula 3 include copper nitrate ($Cu(NO_3)_2$), copper sulfate ($CuSO_4$), copper trifluoromethanesulfonate ($Cu(CF_3SO_3)_2$), ($Cu(ClO_4)_2$), copper halides ($CuX_2$) (X=Cl, Br or I), copper iodide (CuI), copper hydroxide ($Cu(OH)_2$), ($CF_3COO$)Ag, silver sulfate ($Ag_2SO_4$), $Ag(CF_3SO_3)$, $Ag(CF_3SO_3)_2$, silver halides (AgX) (X=Cl, Br or I), silver nitrate ($AgNO_3$), $AgNO_2$, AuCN, $AuX_3$ (X=Cl, Br, I), nickel nitrate ($Ni(NO_3)_2$), $Ni(CF_3SO_3)_2$, $Ni(ClO_4)_2$, and $NiX_2$ (X=Cl, Br, or I).

In another embodiment, a composition for forming metal films or patterns, comprises the organometallic precursor of Formula 1, metal nanoparticles and a solvent. The composition comprising the organometallic precursor of Formula 1, the metal nanoparticles and the solvent is called the organometallic precursor solution.

The metal nanoparticles can be selected from the group consisting of silver (Ag), copper (Cu), nickel (Ni), gold (Au), platinum (Pt), palladium (Pd), iron (Fe), tin (Sn), silicon (Si), magnesium (Mg) and a combination comprising at least one of the foregoing metals.

In one embodiment, the average particle size of the metal nanoparticles can be about 1 nanometer ("nm") to about 100 nm. In another embodiment, the average particle size of the metal nanoparticles can be about 1 nm to about 20 nm.

Examples of solvents that can be used for the composition that contains the nanoparticles can be selected from the group consisting of nitriles such as acetonitrile, propionitrile, pentanenitrile, hexanenitrile, heptanenitrile, and isobutylnitrile; aliphatic hydrocarbons such as hexane, heptane, octane and dodecane; aromatic hydrocarbons such as anisole, mesitylene, and xylene; ketones such as methyl isobutyl ketone, 1-methyl-2-pyrrolidinone, cyclohexanone, and acetone; ethers such as tetrahydrofuran, diisobutyl ether, and isopropyl ether; acetates such as ethyl acetate, butyl acetate, and propylene glycol methyl ether acetate; alcohols such as isopropyl alcohol, butyl alcohol, hexyl alcohol, and octyl alcohol; inorganic solvents; and a combination comprising at least one of the foregoing solvents.

In one embodiment, the metal contained in the organometallic precursor is present in an amount of about 1% to about 50% by weight, based on the total weight of the organometallic precursor. In another embodiment, the metal contained in the organometallic precursor is present in an amount of about 5% to about 30% by weight, based on the total weight of the organometallic precursor.

In addition, the metal nanoparticles contained in the organometallic precursor solution are present in an amount of about 1% to about 90% by weight, based on the total weight of the organometallic precursor solution. When the content of the metal nanoparticles is about 90% by weight or higher, the viscosity of the composition is unsuitable for inkjet printing, spin coating, and the like.

The composition may further comprise a dispersant to maintain dispersion stability by preventing aggregating of the metal nanoparticles. Examples of useful dispersants include polyvinyl pyrrolidone ("PVP"), polyethyleneimine ("PEI"), poly methyl vinyl ether ("PMVE"), polyvinyl alcohol ("PVA"), polyoxyethylene alkyl phenyl ether, polyoxyethylene sorbitan monostearate and derivatives thereof, and a combination comprising at least one of the foregoing dispersants.

Optionally, the composition may further comprise one or more additives depending upon the application that the composition is used for. The adhesion, viscosity, the tail shapes, and wetness of printing heads upon the discharging of ink from the printing head are all parameters that can be modified by adding various additives to the composition.

The composition according to one exemplary embodiment uses both an organometallic precursor and metal nanoparticles, thus leading to an increase in overall metal content and an increase in the thickness of films or patterns. In addition, the organometallic precursor fills voids between nanoparticles, thus forming conductive lines with superior electrical conductivity even when baked at a low-temperature. Further, when the metal contained in the organometallic precursor is different in chemical composition from the metal nanoparticles, baking the composition results in the formation of conductive lines that comprise different alloys.

In another exemplary embodiment, a composition for forming metal films or patterns can comprise the carboxyhydrazide compound of Formula 2, the metal compound of Formula 3 and a solvent.

The composition is prepared by separately dissolving the carboxyhydrazide compound of Formula 2 and the metal compound of Formula 3 in acetonitrile, isopropyl alcohol or methanol and then mixing the resulting solutions with each other at room temperature.

For the composition, the carboxyhydrazide compound of Formula 2 and the metal compound of Formula 3 are mixed in a molar ratio from about 1:1 to about 1:6 respectively and the content of the metal in the composition is about 1% to about 90% by weight, specifically about 5% to about 30% by weight, based on the weight of the composition.

The composition may further comprise metal nanoparticles, a dispersant, additives, and the like, all of which are detailed above.

The use of the organometallic precursor, the composition comprising the precursor, and the composition comprising the carboxyhydrazide and the metal compounds all enable the formation of highly pure metal films or patterns that exhibit high electrical conductivity when baked at low temperatures. The process for manufacturing the metal films or patterns is therefore very simple.

In yet another embodiment, a metal film or pattern can be manufactured using the organometallic precursor or compositions that comprise the organometallic precursor.

More specifically, the organometallic precursor or the composition comprising the organometallic precursor is dissolved in a suitable solvent, and the resulting solution is applied to a substrate and thermally treated at a temperature of about 400° C. or below, specifically at a temperature of about 250° C. or below, and more specifically at a temperature of about 180° C. or below. The organometallic compound is reduced and decomposed to yield a metal film that comprises a highly pure metal. The formation of metal patterns is accomplished by thermal-treating only a predetermined portion of the applied organometallic precursor solution or the composition solution and then developing the same using a predetermined solvent. For example, the partial thermal-treatment can be carried out by using ultraviolet ("UV") treatment though a photomask.

Examples of the solvent that can be used in the dissolution of the organometallic precursor or the composition comprising the organometallic precursor, either prior to or after the formation of patterns include nitriles such as acetonitrile, propionitrile, pentanenitrile, hexanenitrile, heptanenitrile, and isobutylnitrile; aliphatic hydrocarbons such as hexane, heptane, octane and dodecane; aromatic hydrocarbons such as anisole, mesitylene, and xylene; ketones such as methyl isobutyl ketone, 1-methyl-2-pyrrolidinone, cyclohexanone, and acetone; ethers such as tetrahydrofuran, diisobutyl ether, and isopropyl ether; acetates such as ethyl acetate, butyl acetate, and propylene glycol methyl ether acetate; alcohols such as isopropyl alcohol, butyl alcohol, hexyl alcohol, and octyl alcohol; inorganic solvents; and a combination comprising at least one of the foregoing organic solvents.

Materials for use as a substrate upon which the metal patterns can be formed are not particularly limited so long as the function of the metal patterns or the substrate is not impaired. Examples of useful substrate materials include inorganic substrates, e.g., silicon or glass substrates, organic substrates, e.g., plastic substrates, and inorganic-organic complex substrates.

Specific methods for applying the organometallic precursor or the composition comprising the organometallic precursor to the substrate include spin coating, roll coating, deep coating, spray coating, flow coating, electrostatic spray coating, screen printing, or a combination comprising at least one of the foregoing methods of coating. In one exemplary embodiment, it is desirable to use inkjet printing or spin coating.

The thermal-treatment may be carried out in any atmosphere such as nitrogen, air, and the like. A vacuum may also be used while carrying out the thermal treatment. Furthermore, the thermal-treatment may be carried out by soft-baking at a temperature of about 150° C. or below and then annealing at a temperature of about 150° C. to about 300° C.

The organometallic precursor or the compositions comprising the organometallic precursor can be suitably used in any pattern formation method. In one embodiment, it can be applied to direct pattern formation methods using soft-lithography, imprinting, ink-jet printing, silk-screen printing and printing that involves the use of electromagnetic waves (including lasers, electron beams and UV).

The term "soft-lithography" as used herein refers to a technique for transferring patterns of organic compounds or other materials to a substrate using a micro-patterned elastomeric stamp or mold, which encompasses microcontact printing, microtransfer printing, micro molding in capillary ("MIMIC") and solvent-assistance micromolding (See: Younan Xia et. al., Angew. Chem. Int. Ed. 1998, 37, 550-575).

The invention will now be described in further detail with reference to the following examples. These examples are for illustrative purposes only and are not intended to limit the scope of the invention.

EXAMPLES

Preparation Example 1

Synthesis of Organometallic Precursor Compound, $Cu(NO_3)_2[H_2NHNCONHNH_2]$

Copper nitrate ($Cu(NO_3)_2$, 1.87 grams (g), 10 millimoles ("mmol") is dissolved in 5 milliliters ("mL") of acetonitrile in a 50 mL round Schlenk flask, and a solution of carboxyhydrazide ($H_2NHNCONHNH_2$, 0.90 g, 10 mmol) in 5 mL of water is added dropwise to the copper nitrate solution. The reaction is allowed to proceed for one hour with stirring. Then, the reaction mixture in the Schlenk flask is filtered to remove a small amount of impurities. Subsequently, hexane is added to the remaining solution in the Schlenk flask and the solution is precipitated to obtain the target compound, $Cu(NO_3)_2[H_2NHNCONHNH_2]$. The reaction yield for the target compound is 93%.

Preparation Example 2

Synthesis of Organometallic Precursor Compound, $Cu(NO_3)_2[(CH_3OC)HNHNCONHNH(COCH_3)]$ $Cu(NO_3)$ 2 [ $(CH_3OC)HNHNCONHNH(COCH_3)$](the reaction yield for the $Cu(NO_3)_2[(CH_3OC)HNHNCONHNH(COCH_3)]$ is 90%) is synthesized in the same manner as in Preparation Example 1, except that $(CH_3OC)HNHNCONHNH(COCH_3)$ (1.74g, 10 mmol) is used instead of carboxyhydrazide.

Preparation Example 3

Synthesis of Organometallic Precursor Compound, $Au(CN)(n-PrNH_2)[H_2NHNCONHNH_2]$ Gold cyanide (AuCN, 2.23 g, 10 mmol) is dissolved in 10 mL of acetonitrile in a 50 mL round Schlenk flask to form a gold cyanide solution, and a solution of carboxyhydrazide ($H_2NHNCONHNH_2$, 0.90 9, 10 mmol) in 5 mL of water is added dropwise to the gold cyanide solution. Subsequently, propyl amine (1.20 g, 20 mmol) is slowly added dropwise to the mixture, stirred at room temperature for about one hour and the contents of the Schlenk flask are filtered to remove a small amount of impurities. Hexane is added to the solution retained in the Schlenk flask and the solution is precipitated to obtain the target compound, $Au(CN)(n-PrNH_2)[H_2NHNCONHNH_2]$ The reaction yield for the target compound is 80%.

Example 1

Formation of Metal Film Using Organometallic Precursor Compound

Figure 1:
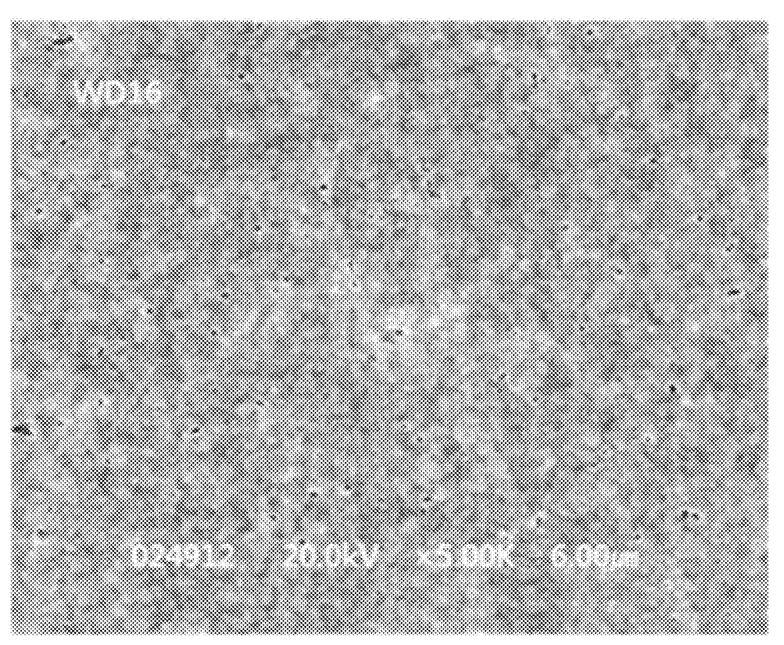
FIG. 1 is a photomicrograph of a scanning electron microscopy ("SEM") image showing morphology of an exemplary embodiment of metal film obtained in Example 1 of the present invention.

Water is added to the organometallic precursor compound ($Cu(NO_3)_2[H_2NHNCONHNH_2]$, 1.0 g, Cu: 0.223 g) synthesized in Preparation Example 1 such that the content of Cu is 10% by weight, based on the total weight of the composition, to prepare a composition (2.23 g). The composition is then spin-coated on to a glass substrate, soft-baked under a nitrogen atmosphere at 150° C. and then annealed at 250° C. to obtain a metal film with a thickness of 1,790 Å. The characteristics of the metal film are analyzed. The results thus obtained are shown in Table 1 below and a SEM image depicting the morphology of the metal film is shown in FIG. 1.

The thickness and specific resistance of the metal film thus obtained were measured with an alpha-step and a four point probe, respectively. The adhesion force of the film thus obtained is measured by 3M tape tests.

Example 2

Formation of Metal Film Using Organometallic Precursor Compound

A metal film having a thickness of 1,579 Å is formed in the same manner as described in Example 1, except that the organometallic precursor compound synthesized in the Preparation Example 2 was used. The characteristics of the metal film thus obtained were analyzed in the same manner as in Example 1. The results thus obtained are shown in Table 1 below.

Example 3

Formation of Metal Film Using Organometallic Precursor Compound

Water is added to the organometallic precursor compound synthesized in Preparation Example 3 to prepare a composition such that the content of Au is 10% by weight, based upon the total weight of the composition. The composition is then spin-coated on to a glass substrate, soft-baked under an atmosphere at 150° C. and then annealed at 200° C. to obtain a metal film having a thickness of 1,904 Å. The characteristics of the metal film were analyzed. The results thus obtained are shown in Table 1 below.

Example 4

Formation of Metal Film Using Composition Comprising Organometallic Precursor Compound and Metal Nanoparticles Water is added to the organometallic precursor compound $(Cu(NO_3)_2[H_2NHNCONHNH_2]$, 1.0 g, Cu: 0.223 g) synthesized in Preparation Example 1 to prepare a composition such that the content of Cu is 10% by weight based on the total weight of the composition $(Cu(NO_3)_2[H_2NHNCONHNH_2]$. Cu nanoparticles (0.223 g, size: 10 nm or less) are dissolved in water such that a total weight of the solution is adjusted to 2.23 g. The Cu nanoparticle solution is mixed with the organometallic precursor compound solution to obtain a composition (4.46 g, Cu: 10 wt %) comprising the organometallic precursor and metal nanoparticles.

The composition is then spin-coated on to a glass substrate, soft-baked under nitrogen at 150° C. and then annealed at 250° C. to obtain a metal film having a thickness of 2,112 Å. The characteristics of the metal film were analyzed. The results thus obtained are shown in Table 1 below.

Example 5

Formation of Metal Film Using Composition Comprising Metal Compound, Carboxyhydrazide Compound and Metal Nanoparticles $Cu(NO_3)_2$ (2.0 g, 10.7 mmol) and Ag nanoparticles (0.27 g, 2.5 mmol, size distribution: 5 to 30 nm) are dispersed in 3.38 g of water, and a solution of carboxyhydrazide (1.35 g, 15 mmol) in water (2.5 ml) is added dropwise to the dispersion to prepare a composition (9.5 g).

The composition is spin-coated to a glass substrate, soft-baked under vacuum at 150° C. and then annealed at 250° C. to obtain a metal film with a thickness of 2,010 Å. The characteristics of the metal film were analyzed. The results thus obtained are shown in Table 1 below.

Comparative Example 1

Formation of Metal Film Using $Cu(NO_3)_2$ Composition

Water is added to $Cu(NO_3)_2$ (1 g, 5.35 mmol, Cu: 0.3388 g) to prepare a composition (3.39 g, Cu: 10 wt %). The composition is then spin-coated on to a glass substrate, soft-baked under nitrogen at 150° C. and then annealed at 250° C. to obtain a metal film having a thickness of 1,885 Å. The characteristics of the metal film were analyzed. The results thus obtained are shown in Table 1 below.

Comparative Example 2

Formation of Metal Film Using Cu Nanoparticle Composition

Water is added to Cu nanoparticles (0.223 g, size: 10 nm or less) to prepare a nanoparticle composition (2.23 g). The composition is then spin-coated on to a glass substrate, soft-baked under nitrogen at 150° C. and then annealed at 250° C. to obtain a metal film with a thickness of 2,107 Å. The characteristics of the metal film were analyzed. The results thus obtained are shown in Table 1 below.

TABLE 1

| | Content of metal (wt %) | Adhesion force | Thickness of film (Å) | Specific resistance ($\mu\Omega \cdot cm$) |
|---|---|---|---|---|
| Ex. 1 | Cu 10 wt % | Pass | 1,790 | 105 |
| Ex. 2 | Cu 10 wt % | Pass | 1,597 | 120 |
| Ex. 3 | Au 10 wt % | Pass | 1,904 | 9 |
| Ex. 4 | Cu 10 wt % | Pass | 2,112 | 100 |
| Ex. 5 | Cu 7.13 wt % Au 2.84 wt % | Pass | 2,010 | 48 |
| Comp. Ex. 1 | Cu 10 wt % | Fail | 1,885 | — |
| Comp. Ex. 2 | Cu 10 wt % | Fail | 2,107 | 178 |

As is apparent from the Table 1, by using the organometallic precursor or compositions according to the exemplary embodiments, highly pure metal films or patterns can be obtained through a simple low-temperature process, regardless of the type of the atmosphere used in the process. The film or pattern thus obtained exhibits superior conductivity and morphology. The film is suitable for use in the field of electric devices including flexible displays and large-screen TFT-LCDs.

The invention has been described in detail with reference to the foregoing exemplary embodiments. However, exemplary embodiments are not limited to the preferred embodiments. Those skilled in the art will appreciate that various modifications and variations are possible, without departing from the scope and spirit of the appended claims.

What is claimed is:

1. An organometallic precursor represented by Formula 1 below:

$$L_nM_mL'_pX_q \quad (1)$$

wherein M is a transition metal; L' is a neutral ligand; X is an anion coordinated or uncoordinated to M; m is an integer of 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q are not zero; L is a carboxyhydrazide compound coordinated to a metal, which is represented by Formula 2:

(2)

wherein $R_1$, $R_2$, $R_3$, $R_4$, $R_5$, and $R_6$ are each independently hydrogen, a substituted or unsubstituted $C_1$-$C_{30}$ alkyl group or a substituted or unsubstituted $C_6$-$C_{30}$ aryl group; G is oxygen, sulfur or $NR_7$, in which N is nitrogen and $R_7$ is hydrogen, a substituted or unsubstituted $C_1$-$C_{30}$ alkyl group or a substituted or unsubstituted $C_6$-$C_{30}$ aryl group; and n is an integer of 1 to about 40, with the proviso that when n is about 2 or higher, L may be identical to or different from each other, and wherein the metal, M is selected from the group consisting of silver, gold, copper, palladium, platinum, osmium, rhodium, cobalt, nickel, cadmium, iridium and iron; L' is a neutral ligand coordinated to a metal, which is a $C_1$-$C_{20}$ organic compound containing an electron-donating atom selected from the group consisting of nitrogen, phosphorus, arsenic, oxygen, sulfur, selenium and tellurium; and X may be coordinated or uncoordinated to a metal compound and is selected from the group consisting of $OH^-$, $CN^-$, $NO_2^-$, $NO_3^-$, trifluoroacetate, tetraalkylborate, tetrahaloborate, hexafluorophosphate, triflate, tosylate, sulfate, carbonate, nitroxyl, azide, acetylacetonate, hydrozino benzoic acid, trifluoroantimonate and combinations thereof.

2. An organometallic precursor represented by Formula 1:

$$L_nM_mL'_pX_q \quad (1)$$

wherein M is a transition metal; L' is a neutral ligand; X is an anion coordinated or uncoordinated to M; m is an integer of 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q are not zero; L is a carboxyhydrazide compound coordinated to a metal, which is represented by Formula 2:

(2)

wherein $R_1$, $R_2$, $R_3$, $R_4$, $R_5$ and $R_6$ are each independently hydrogen, a substituted or unsubstituted $C_1$-$C_{30}$ alkyl group or a substituted or unsubstituted $C_6$-$C_{30}$ aryl group; G is oxygen, sulfur or $NR_7$ in which N is nitrogen and $R_7$ is hydrogen a substituted or unsubstituted $C_1$-$C_{30}$ alkyl group or a substituted or unsubstituted $C_6$-$C_{30}$ aryl group; and n is an integer of 1 to about 40, with the proviso that when n is about 2 or higher, L may be identical to or different from each other wherein the metal, M is selected from the group consisting of silver, gold, copper, palladium, platinum, osmium, rhodium, cobalt, nickel, cadmium, iridium and iron; L' is a neutral ligand coordinated to a metal, which is a $C_1$-$C_{20}$ organic compound containing an electron-donating atom selected from the group consisting of nitrogen, phosphorus, arsenic, oxygen, sulfur, selenium and tellurium; and X may be coordinated or uncoordinated to a metal compound and is selected from the group consisting of $OH^-$, $CN^-$, $NO_2^-$, $NO_3^-$, trifluoroacetate, tetraalkylborate, tetrahaloborate hexafluorophosphate, triflate, tosylate, sulfate, carbonate, nitroxyl, azide, acetylacetonate, hydrozino benzoic acid, trifluoroantimonate and combinations thereof, and wherein the substituent of $R_1$ to $R_7$ is selected from the group consisting of fluoro, chloro, bromo, iodo, hydroxyl, nitrile, nitro, nitrate, nitroxyl, azide, thiocyanate, isothiocyanate, tetraalkylborate, tetrahaloborate, hexafluorophosphate, triflate, tosyl, sulfate, carbonate, thiol, carbonyl, epoxy, vinyl, alkoxy and ester groups.

3. The organometallic precursor according to claim 1, wherein the organometallic precursor represented by Formula 1 is $Cu(NO_3)_2[H_2NHNCONHNH_2]$, $Cu(NO_3)_2[H_2NHNCSNHNH_2]$, $Cu(NO_3)_2(H_2NHNCONHNH_2)(NEt_3)$, $Cu(SO_4)(H_2NHNCONHNH_2)(NEt_3)$, $Cu(NO_3)_2(H_2NHNCSNHNH_2)(NH(n-Bu)_2)$, $Cu(NO_3)_2[CO(NHNHCOCH_3)_2]$, $Cu(NO_3)_2[H_2NHNCONHNHCOC_8H_{17}]$, $Cu(NO_3)_2[CO(NHNHCOC_8H_{17})_2]$, $Ni(NO_3)_2[H_2NHNCONHNH_2]$, $Ni(NO_3)_2[H_2NHNCSNHNH_2]$, $(n-PrNH_2)AuCl_3[H_2NHNCONHNH_2]$, $Au(CN)(NEt_3)[H_2NHNCSNHNH_2]$, or $Au(acetate)[H_2NHNCONHNH_2]$.

4. A composition for forming a metal film or pattern, comprising:
an organometallic precursor represented by Formula 1 below:

$$L_nM_mL'_pX_q \quad (1)$$

wherein M is a transition metal; L' is a neutral ligand; X is an anion coordinated or uncoordinated to a metal;
m is an integer of 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q are not zero; L is a carboxyhydrazide compound coordinated to a metal, which is represented by Formula 2:

(2)

wherein $R_1$, $R_2$, $R_3$, $R_4$, $R_5$, and $R_6$ are each independently hydrogen, a substituted or unsubstituted $C_1$-$C_{30}$ alkyl group or a substituted or unsubstituted $C_6$-$C_{30}$ aryl group; G is oxygen, sulfur or $NR_7$, in which N is nitrogen and $R_7$ is hydrogen, a substituted or unsubstituted $C_i$-$C_{30}$ alkyl group or a substituted or unsubstituted $C_6$-$C_{30}$ aryl group; and n is an integer of 1 to about 40, with the proviso that when n is about 2 or higher, L may be identical to or different from each other; and metal nanoparticles.

5. The composition according to claim 4, wherein the metal constituting the metal nanoparticles is at least one selected from silver, copper, nickel, gold, platinum, palladium, iron, tin, silicon, magnesium and alloys thereof.

6. The composition according to claim 4, wherein the metal contained in the organometallic precursor is present in an amount of about 1 to about 50% by weight, based on the total weight of the organometallic precursor.

7. The composition according to claim 4, wherein the metal nanoparticles in the composition is present in an amount of about 1 to about 90% by weight, based on the total weight of the composition.

8. The composition according to claim 4, wherein the metal nanoparticles have an average particle size of about 1 to about 100 nm.

9. A composition for forming a metal film or pattern, comprising:

a carboxyhydrazide compound represented by Formula 2:

(2)

wherein $R_1$, $R_2$, $R_3$, $R_4$, $R_5$, and $R_6$ are each independently hydrogen, a substituted or unsubstituted $C_1$-$C_{30}$ alkyl group or a substituted or unsubstituted $C_6$-$C_{30}$ aryl group;

G is oxygen, sulfur or $NR_7$, in which N is nitrogen and $R_7$ is hydrogen, a substituted or unsubstituted $C_1$-$C_{30}$ alkyl group or a substituted or unsubstituted $C_6$-$C_{30}$ aryl group;

a metal compound represented by Formula 3:

(3)

wherein M is a transition metal; L' is a neutral ligand; X is an anion coordinated or uncoordinated to M; m is an integer of 1 to about 10, with the proviso that when m is about 2 or higher, M may be identical to or different from each other; and p is an integer of 0 to about 40, and q is an integer of 0 to about 10, with the proviso that when p or q is about 2 or higher, L' or X may be each independently identical to or different from each other, and both p and q are not zero, and further comprising metal nanoparticles.

10. The composition according to claim 9, wherein the carboxyhydrazide compound and the organometallic compound are present in a molar ratio from about 1:1 to about 1:6 respectively.

11. The composition according to claim 9, wherein the content of the metal in the composition is about 1 to about 90% by weight, based on the total weight of the composition.

12. A metal film comprising an organometallic precursor:

the organometallic precursor represented by Formula 1 below:

LnMmL'pXq (1)

wherein M is a transition metal; L' is a neutral ligand; X is an anion coordinated or uncoordinated to M; m is an integer of 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q are not zero; L is a carboxyhydrazide compound coordinated to a metal, which is represented by Formula 2:

(2)

wherein $R_1$, $R_2$, $R_3$, $R_4$, $R_5$, and $R_6$ are each independently hydrogen, a substituted or unsubstituted C1-C30 alkyl group or a substituted or unsubstituted C6-C30 aryl group; G is oxygen, sulfur or NR7, in which N is nitrogen and R7 is hydrogen, a substituted or unsubstituted C1-C30 alkyl group or a substituted or unsubstituted C6-C30 aryl group; and n is an integer of 1 to about 40, with the proviso that when n is about 2 or higher, L may be identical to or different from each other, and wherein the metal, M is selected from the group consisting of silver, gold, copper, palladium, platinum, osmium, rhodium, cobalt, nickel, cadmium, iridium and iron; L' is a neutral ligand coordinated to a metal, which is a C1-C20 organic compound containing an electron-donating atom selected from the group consisting of nitrogen, phosphorus, arsenic, oxygen, sulfur, selenium and tellurium; and X may be coordinated or uncoordinated to a metal compound and is selected from the group consisting of OH—, CN—, NO2—, NO3—, trifluoroacetate, tetraalkylborate, tetrahaloborate, hexafluorophosphate, triflate, tosylate, sulfate, carbonate, nitroxyl, azide, acetylacetonate, hydrozino benzoic acid, trifluoroantimonate and combinations thereof.

13. A metal pattern comprising an organometallic precursor:

the organometallic precursor represented by Formula 1 below:

LnMmL'pXq (1)

wherein M is a transition metal; L' is a neutral ligand; X is an anion coordinated or uncoordinated to M; m is an integer of 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q are not zero; L is a carboxyhydrazide compound coordinated to a metal, which is represented by Formula 2:

(2)

wherein R1, R2, R3, R4, R5, and R6 are each independently hydrogen, a substituted or unsubstituted C1-C30 alkyl group or a substituted or unsubstituted C6-C30 aryl group; G is oxygen, sulfur or NR7, in which N is nitrogen and R7 is hydrogen, a substituted or unsubstituted C1-C30 alkyl group or a substituted or unsubstituted C6-C30 aryl group; and n is an integer of 1 to about 40, with the proviso that when n is about 2 or higher, L may be identical to or different from each other, and wherein the metal, M is selected from the group consisting of silver, gold, copper, palladium, platinum, osmium, rhodium, cobalt, nickel, cadmium, iridium and iron; L' is a neutral ligand coordinated to a metal, which is a C1-C20 organic compound containing an electron-donating atom selected from the group consisting of nitrogen, phosphorus, arsenic, oxygen, sulfur, selenium and tellurium; and X may be coordinated or uncoordinated to a metal compound and is selected from the group consisting of OH—, CN—, NO2—, NO3—, trifluoroacetate, tetraalkylborate, tetrahaloborate, hexafluorophosphate, triflate, tosylate, sulfate, carbonate, nitroxyl, azide, acetylacetonate, hydrozino benzoic acid, trifluoroantimonate and combinations thereof.

14. A metal film comprising a composition for forming a metal film or pattern:
the composition comprising:
an organometallic precursor represented by Formula 1 below:

L$_n$M$_m$L'$_p$X$_q$ (1)

wherein M is a transition metal; L' is a neutral ligand; X is an anion coordinated or uncoordinated to a metal;
m is an integer of 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q.are not zero; L is a carboxyhydrazide compound coordinated to a metal, which is represented by Formula 2:

(2)

wherein R1, R2, R3, R4, R5, and R6 are each independently hydrogen, a substituted or unsubstituted C1-C30 alkyl group or a substituted or unsubstituted C6-C30 aryl group; G is oxygen, sulfur or NR7, in which N is nitrogen and R7 is hydrogen, a substituted or unsubstituted C1-C30 alkyl group or a substituted or unsubstituted C6-C30 aryl group; and n is an integer of 1 to about 40, with the proviso that when n is about 2 or higher, L may be identical to or different from each other; and
metal nanoparticles.

15. A metal film comprising a composition for forming a metal film or pattern,
the composition comprising:
a carboxyhydrazide compound represented by Formula 2:

(2)

wherein $R_1$, $R_2$, $R_3$, $R_4$, $R_5$, and $R_6$ are each independently hydrogen, a substituted or unsubstituted $C_1$-$C_{30}$ alkyl group or a substituted or unsubstituted $C_6$-$C_{30}$ aryl group;

G is oxygen, sulfur or NR$_7$, in which N is nitrogen and R$_7$ is hydrogen, a substituted or unsubstituted $C_1$-$C_{30}$ alkyl group or a substituted or unsubstituted $C_6$-$C_{30}$ aryl group;

a metal compound represented by Formula 3:

M$_m$L'$_p$X$_q$ (3)

wherein M is a transition metal; L' is a neutral ligand; X is an anion coordinated or uncoordinated to M; m is an integer of 1 to about 10, with the proviso that when m is about 2 or higher, M may be identical to or different from each other; and p is an integer of 0 to about 40, and q is an integer of 0 to about 10, with the proviso that when p or q is about 2 or higher, L' or X may be each independently identical to or different from each other, and both p and q are not zero, and
further comprising metal nanoparticles.

16. A metal pattern comprising a composition for forming a metal film or pattern,
the composition comprising:
an organometallic precursor represented by Formula 1 below:

L$_n$M$_m$L'$_p$X$_q$ (1)

wherein M is a transition metal; L' is a neutral ligand; X is an anion coordinated or uncoordinated to a metal;
m is an integer of 1 to about 10, with the proviso that when m is about 2 or higher, M may be identical to or different from each other; p is an integer of 0 to about 40, and q is an integer of 0 to about 10, with the proviso that when p or q is about 2 or higher, L' or X may be each independently identical to or different from each other, and both p and q are not zero; L is a carboxyhydrazide compound coordinated to a metal, which is represented by Formula 2:

(2)

wherein $R_1$, $R_2$, $R_3$, $R_4$, $R_5$, and $R_6$ are each independently hydrogen, a substituted or unsubstituted $C_1$-$C_{30}$ alkyl group or a substituted or unsubstituted $C_6$-$C_{30}$ aryl group; G is oxygen, sulfur or NR$_7$, in which N is nitrogen and R$_7$ is hydrogen, a substituted or unsubstituted

$C_1$-$C_{30}$ alkyl group or a substituted or unsubstituted $C_6$-$C_{30}$ aryl group; and n is an integer of 1 to about 40, with the proviso that when n is about 2 or higher, L may be identical to or different from each other; and metal nanoparticles.

17. A metal pattern comprising a composition for forming a metal film or pattern the composition comprising:

a carboxyhydrazide compound represented by Formula 2:

(2)

wherein $R_1$, $R_2$, $R_3$, $R_4$, $R_5$, and $R_6$ are each independently hydrogen, a substituted or unsubstituted $C_1$-$C_{30}$ alkyl group or a substituted or unsubstituted $C_6$-$C_{30}$ aryl group;

G is oxygen, sulfur or $NR_7$, in which N is nitrogen and $R_7$ is hydrogen, a substituted or unsubstituted $C_1$-$C_{30}$ alkyl group or a substituted or unsubstituted $C_6$-$C_{30}$ aryl group;

a metal compound represented by Formula 3:

$$M_m L'_p X_q \qquad (3)$$

wherein M is a transition metal; L' is a neutral ligand; X is an anion coordinated or uncoordinated to M; m is an integer of 1 to about 10, with the proviso that when m is about 2 or higher, M may be identical to or different from each other; and p is an integer of 0 to about 40, and q is an integer of 0 to about 10, with the proviso that when p or q is about 2 or higher, L' or X may be each independently identical to or different from each other, and both p and q are not zero, and further comprising metal nanoparticles.

* * * * *